United States Patent
Fuller et al.

(10) Patent No.: US 9,615,784 B2
(45) Date of Patent: Apr. 11, 2017

(54) TACTICAL CLINICAL EVALUATION OF PATIENT MONITOR EVENTS

(71) Applicant: General Electric Company, Schenectady, NY (US)

(72) Inventors: Scott Allan Fuller, Milwaukee, WI (US); Stephen Thomas Treacy, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 148 days.

(21) Appl. No.: 14/570,431

(22) Filed: Dec. 15, 2014

(65) Prior Publication Data

US 2016/0171865 A1 Jun. 16, 2016

(51) Int. Cl.
*A61B 5/18* (2006.01)
*A61B 5/00* (2006.01)
*A61B 5/0464* (2006.01)

(52) U.S. Cl.
CPC ............... *A61B 5/18* (2013.01); *A61B 5/746* (2013.01); *A61B 5/7455* (2013.01); *A61B 5/0464* (2013.01)

(58) Field of Classification Search
CPC combination set(s) only.
See application file for complete search history.

(56) References Cited

U.S. PATENT DOCUMENTS

| 2008/0214904 | A1 | 9/2008 | Saeed et al. | |
|---|---|---|---|---|
| 2010/0268157 | A1* | 10/2010 | Wehba | G06F 19/3468 604/66 |
| 2012/0143067 | A1* | 6/2012 | Watson | A61B 5/02108 600/485 |
| 2013/0162424 | A1 | 6/2013 | Treacy | |

FOREIGN PATENT DOCUMENTS

WO 2014/087288 6/2014

OTHER PUBLICATIONS

Visenea (BioSign), http://www.obsmedical.com/products/early-detedtion-patient-monitoring, Apr. 8, 2015, 5 pages.

* cited by examiner

*Primary Examiner* — Kabir A Timory
(74) *Attorney, Agent, or Firm* — Boyle Fredrickson, S.C.

(57) ABSTRACT

In the present invention, a method and accompanying system for evaluating alarm events generated by patient monitors includes the steps of receiving a plurality of alarm events and associated alarm event data from one or more patient monitors at a central control unit, storing the alarm event data in an electronic storage medium, calculating an acuity score for the patient monitor from the alarm event data and a customizable rule set input into and stored in the control unit, the rule set applied to the alarm event data and comparing the calculated acuity score to a threshold value for the acuity score.

15 Claims, 2 Drawing Sheets

TACTICAL CLINICAL EVALUATION OF PATIENT MONITOR EVENTS

BACKGROUND OF THE INVENTION

The invention relates generally to monitoring equipment for illustrating data about a patient to which the equipment is connected, and more particularly to prioritization systems and methods for accurately determining actionable alarms for a patient monitored by the equipment.

In medical monitoring devices that are currently utilized, for the continuous monitoring of patients connected to these devices, data is obtained by the device from various sensors connected to the device. This data is displayed on the monitoring device as numerical values for the various parameters being monitored that are represented on a screen of the device. The clinicians observing the screen and the numerical values represented thereon derive the necessary information by viewing and analyzing the numerical values.

In collecting and formatting the data from the patient for display on the associated screen, the monitoring device can also generate alarms based on sensed events determined by the stored criteria and parameter limits regarding the data collected by the monitoring device and represented by the numerical values. In most situations, the alarms corresponding to the sensed events represented in the data in the displayed are various types of audio and/or visual indicators generated from the monitoring device.

While these devices provide displays and methods of operating the displays that are capable of organizing information relating to various alarm events or conditions for review by an individual, there are a large number of parameters presented on the screen at any given time which are often associated with large numbers of alarms, especially for patients under care in the typical Intensive Care Unit. Due to the large number of the alarm events which may be occurring at a given time across multiple patients being monitored in the care area, certain highly important clinical events could inadvertently be overlooked or missed. This is often referred to as alarm fatigue and results from the constant representation of the alarm events in a similar manner that can cause certain events to become "lost" in the flood of alarms and associated information represented on the display screen of the particular device.

In addition, many of these alarm events are either false positive alarms or are in fact not actionable alarms for the general care area or a specific patient. If this alarm information is not managed by the site, it can further contribute to general alarm fatigue of the patients and staff.

As a result, for situations where the alarm events are in fact true positives, alarm fatigue can contribute to a situation where clinicians failed to identify those patients under care that have adversely trending alarm events. If the patient condition continues to worsen there can be long term injury. Early identification of the specific patients that are deteriorating allows clinical care givers to change their treatment to avoid long term injury.

To address this problem, a number of methodologies for assessing and reporting alarms currently exist and include the following:

1) Clinical Workflows/Personal Vigilance—This system and method relies on clinical workflows for the site, staffing assignments and personal vigilance to properly manage the configuration and patient specific actions that need to be done. This system and method has the limitation that it does not eliminate human error of the clinicians.

2) Early Warning Score (EWS)—This method and system is typically part of a Clinical Decision Support system where a score is created based upon the correlation between observations of a plurality of parameter values for a particular patient. Some systems of this type even allow the end user the ability to configure hard limits or even rates of change to contribute to the score. While these methods and systems can be valuable for identifying the current acuity of the patient, they also have the limitation that the information is essentially provided in the manner of additional notifications in the clinical care area which need to be separately identified and managed by the clinical staff. Additionally, these systems and methods do not address the specific configurations (e.g. alarm limits and level) of the primary method of monitoring patient care which is the patient monitor.

3) Simple data range count—This system and method involves simply counting the number of events occurring over a specified time period (e.g., 4 hours). While limiting the analysis time range is advantageous, there is no ability in these systems and methods to distinguish situations where all the events occurred at the beginning of the specified time period as opposed to all of the events occurring near the end of the specified time period. In former situation the acuity is in fact decreasing, and the later situation the acuity of the patient is increasing, which cannot be determined in this system and method.

In addition, with regard to prior art systems and methods, the alarm events are treated equally in these systems, which does not provide an accurate measure of the significance of any individual alarm events. In particular, depending on the specific workflows of the clinical care area, some alarm events may not be important to the clinical care of the patients, while others are vital. The above existing technologies simply lump the alarm event that occur into very broad categories of assessments without the ability to identify which alarm events are more critical to a particular patient, and thus require additional attention as a result.

In more recent attempts to address the shortcomings of these currently existing systems and methods, a number of alternative alarm metric systems have been developed.

In particular, US Published Patent Application No. US2008/0214904 discloses an apparatus to measure the instantaneous acuity value for a patient. The apparatus and method disclosed utilizes values for monitored physiological parameters and other criteria about the particular patient to create a composite acuity score for the monitored patient based on the underlying preset scoring parameters for the overall system. As the parameters change, the score for the patient can change when the parameters fall out of predetermined ranges for the particular scores associated with that parameter to provide a variable acuity score indicative of the current severity of the condition of the patient, and to trigger any required alarm condition for the patient.

However, while the system of the '904 application provides an enhancement over other prior art systems and methods, that system utilizes preset values and parameter ranges for determining the acuity score for a particular patient. As a result, the system cannot be configured to reflect the needs of a particular care area, and the patients being monitored and treated in that area. Further, the system focuses on the physiological parameters of the patient, and does not account for any potential issues regarding alarm fatigue in the clinical area in which the system is operated.

Further, WO2014/087288 discloses a system and method to reduce nuisance alarm load. The system operates by reviewing the number and types of alarms generated by the patient monitors, and response times for the clinicians to those alarms. Based on the review, the system can determine which patients have exceeded an alarm threshold, either in number of alarms generated or response time for alarms generated, and can send notifications other than alarms to the treating clinicians regarding those patients.

Additionally, US Patent Application Publication No. 2013/0162424, which is expressly incorporated by reference herein in its entirety, discloses a system and method for monitoring clinician responsiveness to alarms. In this system, the response time for clinicians to respond to alarm events generated by patient monitors is determined and used to produce a responsiveness score. The responsiveness score can then be used to further issue enhanced alarms, such as escalated alarms, alarm fatigue notifications.

However, in each of these systems and methods, the system operates only a basis of very simple scoring metric, which is not customizable to the particular care areas in which the system is being utilized. Further, the alarm fatigue determinations in these systems are focused on individual clinicians and their responsiveness to the alarms, rather than with regard to the alarms themselves at a clinical care area level.

Therefore, it is desirable to provide an improved system and method of evaluating patient alarm conditions that incorporates a tailored configuration for patients a care area in which the system is utilized in conjunction with an evaluation of alarm events occurring in the care area to effectively reduce the level of alarm fatigue and increase the effectiveness of patient care in the care area.

BRIEF DESCRIPTION OF THE INVENTION

In the present invention, a system and method for determining an acuity score for a patient being monitored is provided. The system receives alarm signals from a monitoring device operably connected to a patient that relate to the current condition of the patient, as determined by the monitoring device. The signals are utilized by an analytics engine in order to determine the acuity score for the patient. To determine the acuity score, the analytics engine employs a customizable rule set that is adapted to the criteria relevant to the particular care area in which the patient being monitored is being treated. Thus, the rule set can be configured to weight alarms differently, such as by weighting alarms occurring more recently higher that alarms that occurred further in the past. This provides an assessment of a patient based upon real negative trending of the patient condition that is less susceptible to normal deviations in parameter variability.

In the system the analytics engine can also be configured to place different weights or significance on certain alarm conditions sensed by the monitoring device that are of particular relevance to the care area of the patient. As a result of the customization off the rule set employed by the analytics engine, the information concerning the alarm data provided by the analytics engine is displayed at a level corresponding to the particular needs of the clinical care area. As a result, the presentation information by the analytics engine allows for increased visibility of patients condition in the care area and accountability of care of those patients which require additional care.

In addition, using the customized analytics engine the system can provide the acuity scores for each of the patients being monitored in the care area which allows clinical staff in the care area to assess all patients under care, allowing for proper prioritization of staffing.

Further, in the system the analytics engine can use other alarm data, such as the number of audible alarms generated for a particular patient or for the care area, optionally with the response time for responding to the alarms, to determine a score for the entire clinical care area which can be used to assess if the care area is currently susceptible to alarm fatigue.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION OF THE DRAWINGS

In the present description, certain terms have been used for brevity, clarity and understanding. No unnecessary limitations are to be implied therefrom beyond the requirement of the prior art because such terms are used for descriptive purposes only and are intended to be broadly construed. The different systems and methods described herein may be used alone or in combination with other systems and methods. Various equivalents, alternatives, and modifications are possible within the scope of the appended claims. Each limitation in the appended claims is intended to evoke interpretation under 35 USC §112, sixth paragraph, only if the terms "means for" or "step for" are explicitly recited in the respective limitation.

Figure 1:
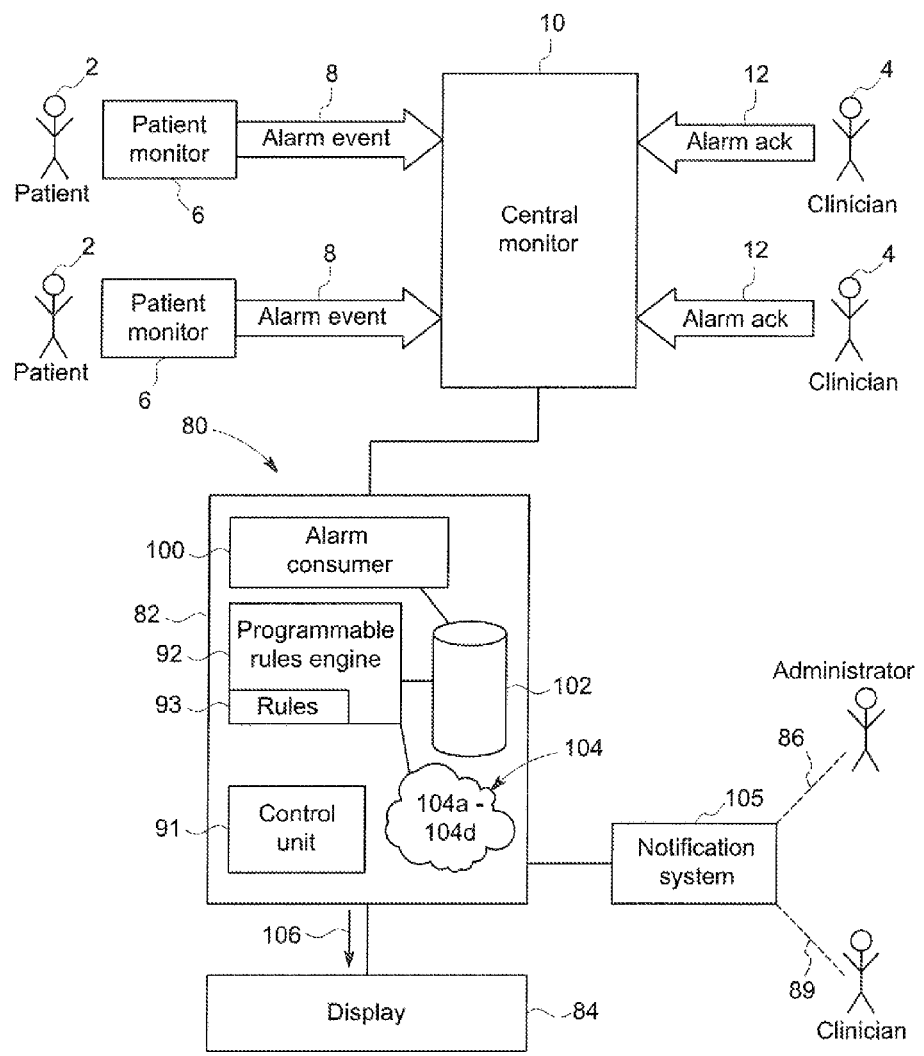
FIG. 1 is a schematic view of a system and method for evaluating patient monitor events according to one embodiment of the present invention.

Referring to FIG. 1, a monitoring system 80 may include a central monitor 10 configured to receive alarm events 8 generated by one or more patient monitors 6 connected to one or more patients 2 in a particular care area, for example, such as an intensive care unit or a neo-natal care unit, among others. The central monitor 10 may also be configured to receive alarm acknowledgements 12 by clinicians 4. The monitoring system 80 may have an analysis unit 82 which processes alarm event data and alarm acknowledgement data acquired by the central monitor and produces an output. The analysis unit 82 can include an alarm consumer 100 that collects all data from the central monitor 10 regarding the alarms 8 generated by the individual patient monitors 6 and stores this information in a suitable electronic storage medium, such as a database 102.

Figure 2:
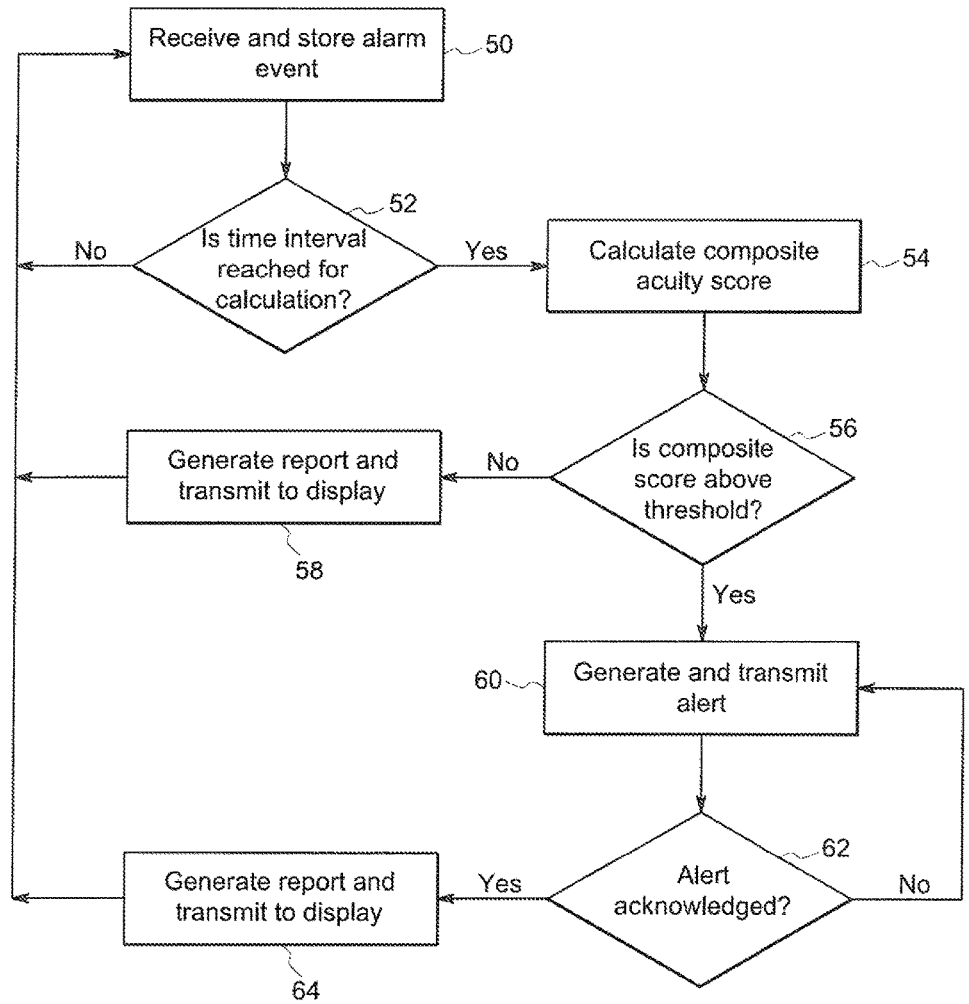
FIG. 2 is a flowchart of the steps performed in a method of evaluating patient monitor events according to one embodiment of the present invention.

The database 102 is operably connected to a control unit 91 in the analysis unit 82 that orchestrates the alarm analysis process. The analysis unit 82 receives data input from the central monitor 10 via the alarm consumer 100 and database 102, including information regarding the alarm events 8 and optionally the alarm acknowledgements 12. The analysis unit 82 processes the data received from the central monitor 10 according to rules established by the programmable analysis engine 92. As depicted in FIG. 2 and explained further below, the programmable analysis engine 92 may contain a set of rules 28 for processing 24 alarm events 8 to provide an output on a display 84. The display 84 may be a central display screen, for example at a nurses' station. Alternatively, the display 84 could be any number of personal displays, including personal computer displays, hand held displays, pagers, or the like. The purpose of the display 84 is to transmit information from the analysis unit or engine 82 to an appropriate nurse administrator or clinician. The central monitor 10 and the analysis unit 82 may be integrated into one device that is controlled by a single control unit, or they may be two separate devices with two separate control units. Likewise, the display unit may be integrated with either the central monitor 10 and/or the analysis unit 82.

The output from the analysis unit 82 may be in form of scores, reports, trends, or any other format known in the art as appropriate for conveying such statistical or qualitative information, and/or can be in the form of various alerts 86, 89 provided to individuals operating and monitoring the system 80.

In the operation of the system 80, the patient monitor 6 collects physiological data from a patient 2 and generates an alarm event 8 upon detection of an alarm condition, such as a detection of an arrhythmia or a monitored physiological parameter for the individual patient that falls outside of a predetermined range for that parameter, among others. The patient monitor 6 may also generate an alarm event 8 if it encounters a technical problem that needs to be remedied by a clinician or other staff member. The alarm events 8 are detected by a central monitor 10. The central monitor 10 may also detect specifics regarding the alarm event, such as the type of alarm generated, the reason for the alarm generation, the time that the alarm was initiated, the severity of the alarm, etc.

The central monitor 10 may also optionally detect when an alarm is acknowledged by a clinician 4. Alarm acknowledgements 12 may be made by a clinician 4 in any way known in the art. For example, clinicians 4 may acknowledge alarms at the patient monitor 6 where the alarm occurred. The alarm acknowledgement 12 may include remedying the condition which generated the alarm event 8. The patient monitor 6 could then detect that the alarm condition has been remedied and could terminate the alarm event 8. For example, in the instance of a technical alarm, such as a low battery in a patient monitor 6, the clinician 4 may remedy the technical alarm by replacing the battery in the patient monitor 6. The patient monitor 6 would then terminate the alarm event 8 generated in response to the low battery alarm. The central monitor 10 may recognize the termination of the alarm event as an alarm acknowledgement 12 by the clinician 4. Alternatively, a clinician 4 may acknowledge 12 an alarm event 8 by clicking on an acknowledgement button on a display screen of the patient monitor 6, or on a display screen at a central monitoring station.

The central monitor 10 relays the alarm event information and/or the alarm acknowledgement information to the analysis unit 82. In the analysis unit 82, the individual alarm events 8 are received by the alarm consumer 100 and stored in the database 102. For each predetermined time period or interval as selected by or programmed into the system 80 by an administrator, the control unit 91 operates the analysis engine 92 to analyze the alarm event information stored in the database 102 for each patient 6 within the care area monitored by the system 80 and determine an acuity score 104 for the individual patients 6.

In determining the acuity score 104, the analysis engine 92 employs a set of rules 93 that are programmed into the analysis engine 92 by an administrator for the system 80 or other suitable individual. The rules 93 are input depending upon the particular criteria that are important for the monitoring of the patients 6 in the specific care area within which the system 80 is operating. Thus, while the monitors 2 for the individual patients 6 are constructed and operable to determine a number of alarm events 8 in view of the data received by the monitors 6 from the patients 2, the analysis engine 92 is configured by the rules 93 to identify only specific alarm events 8 from the monitors 6 as being relevant to the determination of the acuity score 104. For example, in a cardiac care area, alarm events 8 from a monitor 6 relating to any type of arrhythmia in the patient 2 bring monitored are indicated by the rules 93 as being relevant to the acuity score 104, while other ancillary alarm events 8, such as events 8 relating to the temperature of the patient 2, are not considered relevant. In this manner, the rules 93 can be utilized to configure the analysis engine 92 to determine the acuity score 104 based on alarm events 8 particularly relevant to the specific care area, regardless of the overall types of alarm events 8 that are or can be determined by the monitors 6. In this manner, the system 80 can influence a number of aspects that contribute to the occurrence of alarm fatigue by providing a restriction or filter on the types of alarm events 8 that affect the alarm notifications ultimately reaching the clinicians 4 from the system 80 in the site or care area.

After the determination of the relevant alarm events 8 using the constraints provided via the rules 93, the analysis engine 92 may then utilize various criteria related to the relevant alarm events 8 to determine the acuity score 104. These criteria can be provided in the form of an addition to the programmable rules 93 in order to provide an additional level of customization of the system 80 to the particulars of the care area and the individual patients 2 being treated therein. Some examples of the criteria for the relevant alarm events 8 include, but are not limited to, the particular type of relevant alarm event 8, the duration of the alarm event 8, and the severity of the particular alarm event 8, among others.

After determining the acuity scores 104 for the patients 2, the analysis unit 82 compares the scores 104 to score thresholds retained within the analysis unit 82. For any individual scores 104 that exceed the predetermined threshold, indicating a patient 2 in need of additional care, the control unit 91 can provide an output 86, 89 from the system 80 regarding those scores 104. The outputs 86, 89 can be in the form of alerts sent via a suitable notification system 105, such as an in-facility paging system, to a nurse administrator 38 or directly to the clinicians 4.

In addition to any outputs 86, 89 based on the comparison of the acuity scores 104 with the stored internal thresholds, the analysis engine 92 also can produce information summaries and reports regarding the acuity scores 104 for the patients 2 within the monitored care area. The control unit 91 may communicate the scores 104, as well as the reports and/or summaries of the scores 104 to a nurse administrator 38 or other administrator through a display 84 or some other communication device. These reports and summaries can include other information relevant to the acuity scores 104 and/or the patient 2, such as trend data regarding the acuity score 104, trend data regarding one or more of the parameters used in determining the acuity score 104, or any other relevant information.

In one exemplary embodiment of the system 80, the analysis engine 92 determines an acuity score 104 for a patient 2 at predetermined time intervals set for the system 80, for example, every ten (10) minutes or after one (1) hour, depending on the monitoring requirements for the particular care area. In providing the acuity score 104 at each interval, such as to determine a composite acuity score 106, the analysis engine 92 will calculate a number of separate acuity scores, for example, acuity scores 104a, 104b, and 104c for the various types of relevant alarm events 8 that have been received by the alarm consumer 100 and stored in the database 102 over a selected determination time period prior to the operation of the analysis engine 92, which in an exemplary embodiment for a cardiac care area are identified as the arrhythmia (104a), parameter (104b) and technical (104c) alarm events 8 generated by a specific patient monitor 6. In other situations, such as for different patients and/or care areas, the general types of alarm events 8, such as the arrhythmia events, can be replaced by other relevant events, and/or the individual parameters selected as being relevant for the parameter alarm events 8 to be utilized can be modified as necessary or desired using the programmed rules 93 for the system 80.

The composite acuity score 106, or individual component scores 104a-104c, could be expressed on the display 84 or transmitted or communicated to a suitable device according to any scale or system. For example, the score 106 could be expressed on a 1 to 10 scale, or on a traditional A to F grading scale. In other embodiments, the composite acuity score 106 could be more nuanced and convey more detailed information. For example, the score 106 could have multiple parts or sections, each conveying information about different types of alarm events or alarm events occurring at different times during the determination time period. In still other embodiments, the score 106 could be a sliding scale with one end representing no current care required for a patient 2 and the other end representing an urgent need for such care for a patient 2. Such a sliding scale could account for any number of rules 93, and thus could represent a varying level of complexity based on the configuration of the programmable analysis engine 92.

These individual scores 104a, 104b, 104c can be calculated in any suitable manner, but in an exemplary embodiment are calculated based on the number of each type of alarm event 8 occurring over the relevant determination time period. The determination time period can be selected to be the same as or different from the time intervals at which the system 80 calculates the acuity scores 104a, 104b, 104c, and in an exemplary embodiment the determination time period is selected to be the four (4) hours prior to the acuity score calculation. Alternatively, the determination time period can be selected by the user of the system 80 to be between two (2) to eight (8) hours. An arithmetic sum for these scores 104a, 104b, 104c will be used to generate a composite acuity score 106 for the defined determination time period over which the analysis engine 92 review the alarm events 8 received by the monitor 6 and stored in the database 102, as shown in the below exemplary formula:

$$AS_{comp} = AS_{arr} + AS_{parm} + AS_{tech}$$

Upon generation of the composite acuity score 106, the analysis engine 92 subsequently compares the composite score 106 against a stored threshold for the composite score to assess the current status of the patient(s) 2 and whether any of the patients 2 requires any additional care. If the composite scores 106 exceed the threshold, notices 86, 89 concerning the scores 106 for the particular patients 2 are sent out from the system 80. For example, the alerts or notices 86, 89 may be transmitted to the appropriate individual through an auditory alarm, a visual alarm, a notification on a display, or through a personal device, such as a pager or a PDA.

In another exemplary embodiment for the system 80, the system 80 can be further customized and/or adapted for use in a particular care area to enhance the ability of the system 80 to provide accurate negative trend information about the conditions of patients 2 in the care area that is less susceptible to normal deviations in parameter viability and that provides increased visibility and accountability of the conditions of those patients 2 to enable clinical staff in the care area to properly prioritize those patients 2 in need of care. In this embodiment, when calculating the composite acuity score 106, the individual acuity scores 104a, 104b and 104c are each determined using weighted criteria related to the relevant alarm events 8 for each of the acuity scores 104a, 104b, 104c. These criteria can be provided in the form of a weighting algorithm in the programmable rules 93. In one exemplary embodiment, the weighting provided by the rules 93 can take the form of a multiplier for certain alarm events 8 of any of the types used to determine the composite score 106. In one situation, for a system 80 employed in a cardiac or intensive care area, any ventricular tachycardia (VTACH) events that occurred in the relevant determination time period are multiplied by a factor of 2.5 to increase the significance of these types of events 8 in the arrhythmia acuity score 104a used in computing the ultimate composite acuity score 106. As a result, if the analysis engine 92 determined that two (2) such events 8 occurred in the relevant determination time period, the acuity score 104a would include a value of five (5), which is equal to 2.5 (the multiplier)×2 (the number of VTACH events 8), in addition to the values for any other events 8 used in calculating the acuity score 104a.

Conversely, the weighting used in the rules 93 can also be employed to de-emphasize certain events 8, of any type used to compute the scores 104a, 104b, 104c and 106. In the previous exemplary embodiment, for example, in order to reduce or ignore the effect of any atrial fibrillation (AFIB) event configured at only a visual only or non-audible level on the arrhythmia acuity score 104a, the multiplier used for these types of events 8 can be set at zero (0). As such, if the analysis engine 92 determined that two (2) such events 8 occurred in the relevant determination time period, the acuity score 104a would include a value of zero (0), which is equal to 0 (the multiplier)×2 (the number of AFIB events 8), in addition to the values for any other events 8 used in calculating the acuity score 104a.

In another exemplary embodiment of the invention, either as an alternative to or in conjunction with the weighting rules from the prior discussed exemplary embodiments of the system 80, the rules 93 can include weighting factors for individual time periods within the determination time period used for the calculation of the composite acuity score 106. For example, in reviewing the stored event 8 in the database 102 from the relevant determination time period, the rules 93 can direct the analysis engine 92 to weight the events 8 occurring in each of the four hours of the determination time period differently, in order to provide a greater significance to those events 8 that have occurred in the most recent hours of the determination time period. This weighting scheme will accentuate patients with a higher recent composite acuity score 106 and lower the composite score 106 for patient monitors that have already "been corrected" or have been improving over the particular determination time period. In particular, for the composite acuity score 106, the analysis engine 92 can apply the following formula provided by the rules 93 programmed into the system 80:

$$AS_{score} = (AS_{comp}[t_1])*2.50) + (AS_{comp}[t_2])*1.0) + (AS_{comp}[t_3])*0.5) + (AS_{comp}[t_4])*0.1)$$

Using this formula, the analysis engine 92 will output a composite acuity score 106 that places significantly more emphasis (2.5 times) on a calculated composite acuity score 106 for the most recent hour ($t_1$) of the determination time period while placing much less emphasis (0.1 times) on a calculated composite acuity score 106 for the earliest hour ($t_4$) of the determination time period. This time-based weighting scheme can also be utilized when calculating the individual event acuity scores 104a-104c over the same determination time period.

In addition to the above exemplary embodiments, the rules 93 provided for implementation by the analysis unit or engine 92 of the system 80 can include other modifications can be made as alternatives or additions to the above rules 93. For example, the composite score 106 can include an additional acuity component score 104d that is based on: 1.) a non-weighted alarm event tally for the determination time period; 2.) a tally of audible alarm events that occurred in the determination time period; or 3.) alarm response times as determined in any suitable manner. Further, the individual component acuity scores 104a-104d can also incorporate the duration (start-end) of events 8 into the calculation, such as by providing increased emphasis on events 8 lasting over a specified time duration, or third party information, including, but not limited to, staff interactions with the system 80 using suitable communication devices, such as Vocera® devices or suitable paging devices, which can be useful in determining alarm response times as a component acuity score and for the determination of alarm fatigue.

Referring to FIG. 2, the flowchart depicts one embodiment of a method of evaluating alarm events 8 generated by the patient monitors 6 in a clinical care area. Initially, an alarm event 8 generated by the monitor 6 is received and stored by the alarm consumer 100 of the system 80 in the database 102 at block 50. The alarm event data received may include details regarding the alarm event, including the type of alarm that generated the event, the criticality or severity of the condition that generated the alarm, and/or the initiation time of the alarm. After receiving and storing the alarm event at block 50, in decision block 52 the control unit 91 for the system 80 may determine whether a specified time interval for reviewing the stored alarm event data has elapsed. If the time interval has not elapsed, the control unit 91 proceeds back to block 50 where the system 80 continues to receive and store additional alarm event data provided to the system 80 by the patient monitors 6. However, if the time interval has elapsed, in block 54 the system 80 operates the analysis unit 92 to review and analyze the alarm event data stored in the database 102 in accordance with the rules 93 programmed into the system 10 to determine acuity scores for the patients 2 having monitors 6 supplying alarm event data to the system 80.

Once the analysis unit 92 has calculated the acuity scores 106, in decision block 56 the analysis unit 92 compares the acuity cores 106 to the stored thresholds to assess whether any of the calculated scores 106 exceed the threshold value. If none of the scores 106 are above the threshold, the system 80 proceeds to block 58 to create a report for the review data that can be communicated to the display 84 for review by the care area staff. The system 80 then returns to block 50 to receive and store additional alarm event data during the subsequent interval prior to initialing another analysis of the stored data.

However, if the analysis unit 92 determines that one or more of the acuity scores 106 exceed the threshold, in block 60 the control unit 91 generates an alert 86,89 that is transmitted to the care area staff 4,38 to communicate the need for immediate attention to the patient(s) 2 having the elevated acuity score(s) 106. The system 80 then proceeds to decision block 62 to determine whether an acknowledgement of the alert has been received from the staff. If not, the system 80 returns to block 60 re-issue or maintain the alert 86, 89 until receiving the acknowledgement. Once the acknowledgement is received, the system 80 prepares a report in block 64 on the analyzed alarm event data along with the information concerning the specific alert(s) 86, 89 that were generated and transmits this report to a display 84 or other device for review and further analysis by the care area staff. After transmitting the report, the system 80 returns to block 50 to receive and store additional alarm event data during the next time interval prior to a subsequent analysis being initiated.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of evaluating alarm events generated by patient monitors, the method comprising the steps of:
    a) receiving a plurality of alarm events and associated alarm event data from one or more patient monitors at a central control unit;
    b) storing the alarm event data in an electronic storage medium;
    c) selecting a time interval for performing the step of calculating an acuity score;
    d) calculating an acuity score for the patient monitor from the alarm event data and a customizable rule set input into and stored in the control unit, the customizable rule set applied to the alarm event data relevant to a care area in which the patient monitors are located;
    e) comparing the calculated acuity score to a threshold value for the acuity score;
    f) transmitting an alert if the acuity score exceeds the stored threshold value;
    g) re-calculating the acuity score upon expiration of each time interval; and
    h) transmitting an alert if the re-calculated acuity score exceeds the stored threshold value,
    wherein the step of calculating the acuity score comprises applying a weighting factor from the customizable rule set to the alarm event data, and
    wherein the step of applying a weighting factor to the alarm event data comprises:
        i) increasing a significance of a first portion of the alarm event data; and
        ii) decreasing significance of second portion of the alarm event data.

2. The method of claim 1 further comprising the step of selecting a determination time period over which the stored alarm event data is received for calculation of the acuity score.

3. The method of claim 2 wherein the time interval and the determination time period are not equal.

4. The method of claim 1 wherein the weighting factor is a factor applied as a result of the severity of the alarm event.

5. The method of claim 1 wherein the weighting factor is a factor applied as a result of a duration of the alarm event.

6. The method of claim 1 wherein the weighting factor is a factor applied as a result of a type of the alarm event.

7. The method of claim 1 wherein the weighting factor is a factor applied as a result of when the alarm event occurred in a determination time period.

8. The method of claim 7 wherein the step of applying the weighting factor to the alarm event data comprises more significantly weighting alarm events occurring more recently within the determination time period.

9. The method of claim 1 wherein the step of calculating the acuity score comprises:
   a) calculating a customized alarm event acuity score in conjunction with the customized rule set;
   b) calculating a customized parameter alarm event acuity score in conjunction with the customized rule set; and
   c) summing the customized alarm event acuity score and the customized parameter alarm event acuity score to form a composite acuity score.

10. The method of claim 9 further comprising the steps of:
    a) generating a report including the calculated composite acuity score; and
    b) transmitting the report to a display device for viewing by a clinician.

11. The method of claim 9 further comprising the steps of:
    a) calculating a customized technical alarm event acuity score in conjunction with the customized rule set; and
    b) summing the customized alarm event acuity score, the customized parameter alarm event acuity score and the customized technical alarm event acuity score in conjunction with the customized rule set to form a composite acuity score.

12. A method of evaluating a patient condition from alarm events generated by patient monitors, the method comprising the steps of:
    a) inputting a customized rule set into a central control unit including at least one weighting factor applied to alarm event data relevant to a care area in which the patient monitors are located;
    b) receiving and storing at a central monitor a notification of an alarm event and associated alarm event data from a patient monitor;
    c) selecting a time interval for performing the step of calculating an acuity score;
    d) calculating an acuity score from the alarm event data and the customized rule set;
    e) comparing the acuity score to an acuity score threshold value to determine a patient condition; and
    f) transmitting the calculated acuity score and the patient condition for review by a clinician;
    g) generating an alert if the acuity score exceeds the stored threshold value;
    h) re-calculating the acuity score upon expiration of each time interval; and
    i) generating an alert if the re-calculated acuity score exceeds the stored threshold value;
    wherein the step of calculating the acuity score comprises applying a weighting factor from the customizable rule set to the alarm event data, and
    wherein the step of applying a weighting factor to the alarm event data comprises:
        i) increasing a significance of a first portion of the alarm event data; and
        ii) decreasing significance of second portion of the alarm event data.

13. The method of claim 12 wherein the step of calculating the acuity score comprises:
    a) calculating a customized alarm event acuity score in conjunction with the customized rule set;
    b) calculating a customized parameter alarm event acuity score in conjunction with the customized rule set;
    c) calculating a customized technical alarm event acuity score in conjunction with the customized rule set; and
    d) summing the customized alarm event acuity score, the customized parameter alarm event acuity score and the customized technical alarm event acuity score in conjunction with the customized rule set to form a composite acuity score.

14. The method of claim 13 further comprising the step of selecting a determination time period over which the stored alarm event data is received for calculation of the customized alarm event acuity score, the customized parameter alarm acuity score and the customized technical alarm event acuity score.

15. A system for evaluating alarms events determined by a patient monitor, the system comprising:
    a) a patient monitor configured to receive physiological patient data, to detect an occurrence of an alarm condition, and to transmit an alarm event notification of the alarm condition and accompanying data concerning the alarm event;
    b) a control unit configured to receive the notification of the alarm and accompanying data, to calculate an acuity score within a selected time interval with the data from the patient monitor and a customizable weighted rule set input into the control unit to customize the acuity score to a clinical care area within which the system is operated, to store the acuity score on a computer-readable memory device, to re-calculate an acuity score within a subsequent selected time interval with the data from the patient monitor and a customizable weighted rule set, to apply a weighting factor from the customizable rule set to the alarm event data to increase a significance of a first portion of the alarm event data and decrease a significance of second portion of the alarm event data, and to generate an alert if one of the calculated acuity score or the re-calculated acuity score exceeds a stored threshold value for the acuity score.

* * * * *